(12) United States Patent
Kravtchenko et al.

(10) Patent No.: US 7,682,402 B2
(45) Date of Patent: Mar. 23, 2010

(54) AQUEOUS COMPOSITION COMPRISING HYDROGEN PEROXIDE AND INERT PARTICLES

(75) Inventors: Sylvain Kravtchenko, Shanghai (CN); Claude Dubief, Le Chesnay (FR)

(73) Assignee: L'Oreal, S.A., Paris (FR)

( * ) Notice: Subject to any disclaimer, the term of this patent is extended or adjusted under 35 U.S.C. 154(b) by 0 days.

(21) Appl. No.: 11/918,050

(22) PCT Filed: Apr. 7, 2006

(86) PCT No.: PCT/EP2006/003980

§ 371 (c)(1),
(2), (4) Date: Feb. 7, 2008

(87) PCT Pub. No.: WO2006/106000

PCT Pub. Date: Oct. 12, 2006

(65) Prior Publication Data

US 2009/0031505 A1 Feb. 5, 2009

Related U.S. Application Data

(60) Provisional application No. 60/670,267, filed on Apr. 12, 2005.

(30) Foreign Application Priority Data

Apr. 7, 2005 (FR) .................................. 05 50897

(51) Int. Cl.
*D06L 3/02* (2006.01)
(52) U.S. Cl. .................. 8/111; 8/405; 8/406; 8/407; 8/102
(58) Field of Classification Search .......... 8/111, 8/45, 406, 407, 102, 103, 405
See application file for complete search history.

(56) References Cited

U.S. PATENT DOCUMENTS

| | | | |
|---|---|---|---|
| 2,528,378 A | 10/1950 | Mannheimer | |
| 2,781,354 A | 2/1957 | Mannheimer | |
| 3,726,967 A | 4/1973 | Vorsatz et al. | |
| 3,915,921 A | 10/1975 | Schlatzer, Jr. | |
| 4,003,699 A | 1/1977 | Rose et al. | |
| 4,509,949 A | 4/1985 | Huang et al. | |
| 4,540,510 A | 9/1985 | Karl | |
| 5,061,289 A | 10/1991 | Clausen et al. | |
| 5,089,578 A | 2/1992 | Valint et al. | |
| 5,380,340 A | 1/1995 | Neunhoeffer et al. | |
| 5,534,267 A | 7/1996 | Neunhoeffer et al. | |
| 5,663,366 A | 9/1997 | Neunhoeffer et al. | |
| 5,708,151 A | 1/1998 | Mockli | |
| 5,766,576 A | 6/1998 | Lowe et al. | |
| 5,824,296 A | 10/1998 | Dubief et al. | |
| 6,099,592 A | 8/2000 | Vidal et al. | |
| 6,099,593 A | 8/2000 | Terranova et al. | |
| 6,284,003 B1 | 9/2001 | Rose et al. | |
| 6,540,791 B1 * | 4/2003 | Dias | 8/111 |
| 6,730,789 B1 | 5/2004 | Birault et al. | |
| 6,740,619 B1 | 5/2004 | Puri et al. | |
| 6,822,039 B1 | 11/2004 | Monfreux-Gaillard et al. | |
| 2002/0176843 A1 | 11/2002 | Creton | |
| 2003/0124079 A1 | 7/2003 | Mougin et al. | |

FOREIGN PATENT DOCUMENTS

| | | |
|---|---|---|
| DE | 2 205 461 | 8/1973 |
| DE | 23 59 399 | 6/1975 |
| DE | 38 43 892 | 6/1990 |
| DE | 41 33 957 | 4/1993 |
| DE | 195 43 988 | 5/1997 |
| EP | 0 033 687 | 8/1981 |
| EP | 0 173 109 | 3/1986 |
| EP | 0 216 479 | 2/1991 |
| EP | 0 714 954 | 6/1996 |
| EP | 0 750 899 | 1/1997 |
| EP | 0 770 375 | 5/1997 |
| FR | 2 044 324 | 2/1971 |
| FR | 2 633 940 | 1/1990 |
| FR | 2 733 749 | 11/1996 |
| FR | 2 750 048 | 12/1997 |
| FR | 2 801 308 | 5/2001 |
| FR | 2 811 993 | 1/2002 |
| FR | 2 816 854 | 5/2002 |
| GB | 1026978 | 4/1966 |

(Continued)

OTHER PUBLICATIONS

Aerosil® 380 Product Information.

(Continued)

*Primary Examiner*—Eisa B Elhilo
(74) *Attorney, Agent, or Firm*—Finnegan, Henderson, Farabow, Garrett & Dunner, LLP

(57) ABSTRACT

The present invention relates to an aqueous composition for bleaching keratin fibers, and in particular human keratin fibers such as the hair, having a viscosity of less than $2 \times 10^3$ poises and comprising, in a cosmetically acceptable medium, hydrogen peroxide and at least 20% by volume of suitably selected inert particles, to a bleaching process using this composition, and also to the use of this composition for bleaching keratin fibers. The composition in accordance with the invention makes it possible rapidly to obtain substantial lightening of keratin fibers, while at the same time limiting the degradation of the keratin fibers and the skin irritation.

20 Claims, No Drawings

FOREIGN PATENT DOCUMENTS

| | | |
|---|---|---|
| GB | 1153196 | 5/1969 |
| JP | 2-19576 | 1/1990 |
| WO | WO 94/08969 | 4/1994 |
| WO | WO 94/08970 | 4/1994 |
| WO | WO 95/01772 | 1/1995 |
| WO | WO 95/15144 | 6/1995 |
| WO | WO 96/15765 | 5/1996 |
| WO | WO 98/44012 | 10/1998 |
| WO | WO 00/31154 | 6/2000 |

OTHER PUBLICATIONS

Aerosil® R 972 Product Information.
Color Index International, $3^{rd}$ Edition, (1988).
CTFA Dictionary, 3rd Edition (1982).
CTFA Dictionary, $5^{th}$ Edition (1993).
Davidson, Robert L., "Handbook of Water Soluble Gums And Resins," *McGraw Hill Book Company* (1980).
Derwent English Abstract for DE 2 205 461, Week 197335.
Derwent English Abstract for EP 0 033 687, Week 198134.
Derwent English Abstract for EP 0 770 375, Week 199722.
Derwent English Abstract for FR 2 633 940, Week 199009.
Derwent English Abstract for JP 2-19576, Week 199009.
Derwent English Abstract for RU 2 066 179, 1997-211154.
Fonnum, G. et al., "Associative thickeners. Part I: Synthesis, rheology and aggregation behavior," *Colloid Polymer Science*, 271:380-389 (1993).
International Search Report for PCT/EP2006/003980 dated Aug. 29, 2006.
Morishima, Yaotaro, "Self-Assembling Amphiphilic Polyelectrolytes And Their Nanostructures," *Chinese Journal of Polymer Science*, 18(40):323-336 (2000).
Noda, T. et al., "Solution Properties of Micelle Networks Formed by Nonionic Surfactant Moieties Covalently Bound to a Polyelectrolyte: Salt Effects on Rheological Behavior," *Langmuir*, 16(12):5324-5332 (2000).
Noda, T. et al. "Stimuli Responsive Amphiphilic Copolymers Of Sodium 2-(Acrylamido)-2-Methylpropanesulfonate And Associative Macromonomers," *Polymer Preprint, Div. Polymer Chemical*, 40(2):220-221 (1999).
Noda, T. et al. "Micelle Formation of Random Copolymers of Sodium 2-(Acrylamido)-2-methylpropanesulfonate and a Nonionic Surfactant Macromonomer in Water As Studied by Fluorescence and Dynamic Light Scattering," *Macromolecules*, 33(10):3694-3704 (2000).
Porter, M. R., "Handbook Of Surfactants," *Blackie & Son* (Glasgow and London), pp. 116-178 (1991).

\* cited by examiner

AQUEOUS COMPOSITION COMPRISING HYDROGEN PEROXIDE AND INERT PARTICLES

CROSS REFERENCE TO RELATED APPLICATIONS

This application is a national phase application based on PCT/EP2006/003980, filed on Apr. 7, 2006, and claims the benefit of U.S. Provisional Application No. 60/670,267, filed on Apr. 12, 2005, and the priority of French Patent Application No. 0550897, filed Apr. 7, 2005, all of which are incorporated herein by reference in their entirety.

The present invention relates to an aqueous composition for bleaching keratin fibres, and in particular human keratin fibres such as the hair, comprising hydrogen peroxide and suitably selected inert particles.

When a person wishes to radically change his hair colour, especially when he wishes to obtain a colour lighter than his original colour, it is often necessary to bleach the hair. Bleaching products are used to do this. This bleaching step is optionally combined with a step of dyeing the hair.

It is known practice to bleach keratin fibres, and in particular human keratin fibres such as the hair, with bleaching compositions containing one or more oxidizing agents. Among the oxidizing agents conventionally used, mention may be made of hydrogen peroxide, compounds capable of producing hydrogen peroxide by hydrolysis, such as urea peroxide, or persalts, for instance perborates, carbonates and persulfates, hydrogen peroxide and persulfates being particularly preferred.

Bleaching compositions are mainly in the form of anhydrous products, powders or creams, containing alkaline compounds such as amines or alkaline silicates, and a peroxygenated reagent such as ammonium or alkali metal persulfates, perborates or percarbonates, which are diluted at the time of use with an aqueous hydrogen peroxide composition.

Bleaching compositions may also result from mixing, at the time of use, an anhydrous powder containing the peroxygenated reagent with an aqueous composition containing the alkaline compounds and another aqueous composition containing the hydrogen peroxide.

Bleaching compositions are also presented in the form of thickened aqueous hydrogen peroxide compositions.

To obtain a keratin fibre bleaching product that is more efficient, for example which makes it possible to obtain greater or faster lightening, one solution consists in increasing the concentration of hydrogen peroxide in the aqueous hydrogen peroxide composition. However, a high concentration of hydrogen peroxide results in appreciable degradation of the keratin fibres and skin irritation. The hydrogen peroxide concentration is thus conventionally limited to 12% by weight or even to 6% by weight relative to the total weight of the aqueous hydrogen peroxide composition.

The aim of the present invention is to provide novel bleaching products that are more efficient than the known products of the prior art, while at the same time limiting the degradation of keratin fibres and the skin irritation.

This aim is achieved with the present invention, one subject of which is an aqueous composition for bleaching keratin fibres, which has a viscosity of less than $2 \times 10^3$ poises and which comprises, in a cosmetically acceptable medium, hydrogen peroxide and at least 20% by volume of suitably selected inert particles.

The composition in accordance with the invention makes it possible rapidly to obtain substantial lightening of keratin fibres, while at the same time limiting the degradation of the keratin fibres and the skin irritation. Specifically, the inert particles present in the composition in accordance with the invention make it possible to obtain substantial lightening with reasonable concentrations of hydrogen peroxide.

A subject of the present invention is also a process for bleaching keratin fibres using the composition in accordance with the invention, and also multi-compartment devices for performing this process.

Another subject of the invention is the use of the composition in accordance with the invention for bleaching keratin fibres.

In the context of the invention, the viscosity of the composition in accordance with the present invention is measured using a Rheomat 180 viscometer, at a temperature of 25° C. and with a shear rate of $1\ s^{-1}$. It is preferably between 0.1 and $2 \times 10^3$ poises, even more preferentially between 1 and $10^3$ poises and even more preferentially between 5 and 300 poises.

In the context of the present invention, the term "inert particles" means any mineral, plant or synthetic particles that are insoluble in the medium, of any form, solid, hollow or porous, which are chemically inert with respect to the oxidizing agent. The degradation of hydrogen peroxide in the presence of these particles is less than 25% after 15 hours at 100° C.

In the context of the invention, the inert particles are chosen from titanium oxides, zinc oxides, carbonates, silicates, sulfides, polyamides, polyesters, polystyrenes, polyurethanes, polycyanoacrylates, polyethylenes, polymethyl methacrylates, polypropylenes, polycarbonates, Teflon, silicone resins, silicone elastomers, waxes and complex synthetic compounds, and mixtures thereof.

Examples of polyamides that may be mentioned include polyamides 6, polyamides 66 and polyamides 11, and mixtures thereof.

Examples of complex synthetic compounds that may be mentioned include ceramic powders, zeolites and glasses, and mixtures thereof.

The size of the inert particles that are useful in the context of the present invention is generally between 5 nm and 500 µm and preferably between 10 nm and 100 µm.

The inert particles may be used in unmodified form or may be surface-modified beforehand by adsorption or grafting of molecules or macromolecules in order to obtain different physicochemical surface properties.

The hydrogen peroxide concentration in the composition in accordance with the invention is generally between 1% and 20% and preferably between 2% and 12% by weight relative to the total weight of the composition.

The composition of the invention may furthermore comprise dispersion stabilizers. These agents are, for example, surfactants or associative or non-associative thickening polymers.

The composition of the invention may comprise, for example, as stabilizers at least one surfactant with at least one fatty chain containing at least 8 and preferably between 8 and 22 carbon atoms. The surfactants may be anionic, amphoteric or zwitterionic, nonionic and cationic.

As examples of anionic surfactants that may be used, alone or as mixtures, in the context of the present invention, mention may be made in particular (non-limiting list) of salts (in particular alkali metal salts, especially sodium salts, ammonium salts, amine salts, amino alcohol salts or magnesium salts) of the following compounds: alkyl sulfates, alkyl ether sulfates, alkylamido ether sulfates, alkylarylpolyether sulfates, monoglyceride sulfates; alkyl sulfonates, alkyl phosphates, alkylamide sulfonates, alkylaryl sulfonates, α-olefin sulfonates, paraffin sulfonates; alkyl sulfosuccinates, alkyl ether sulfosuccinates, alkylamide sulfosuccinates; alkyl sulfoacetates; acyl sarcosinates and acyl glutamates. It is also possible to use alkylpolyglycoside carboxylic esters such as alkylglucoside citrates, alkylpolyglycoside tartrates and alkylpolyglycoside sulfosuccinates, alkylsulfosuccinamates; acyl isethionates and N-acyl taurates.

The alkyl or acyl radical of all of these different compounds preferably contains from 12 to 20 carbon atoms and the aryl radical preferably denotes a phenyl or benzyl group.

Among the anionic surfactants that may also be used, mention may also be made of fatty acid salts such as oleic, ricinoleic, palmitic and stearic acid salts, coconut oil acid or hydrogenated coconut oil acid; acyl lactylates in which the acyl radical contains 8 to 20 carbon atoms. It is also possible to use alkyl D-galactoside uronic acids and their salts, polyoxyalkylenated alkyl ether carboxylic acids, polyoxyalkylenated alkylaryl ether carboxylic acids, polyoxyalkylenated alkylamido ether carboxylic acids and their salts, in particular those containing from 2 to 50 alkylene oxide groups in particular ethylene oxide groups, and mixtures thereof.

The nonionic surfactants are, themselves also, compounds that are well known per se (see in particular in this respect "Handbook of Surfactants" by M. R. Porter, published by Blackie & Son (Glasgow and London), 1991, pp. 116-178). Thus, they can be chosen in particular from polyethoxylated, polypropoxylated, alkylphenols, alpha-diols or alcohols having a fatty chain containing, for example, 8 to 18 carbon atoms, it being possible for the number of ethylene oxide or propylene oxide groups to range in particular from 2 to 50. Mention may also be made of copolymers of ethylene oxide and of propylene oxide, condensates of ethylene oxide and of propylene oxide with fatty alcohols; polyethoxylated fatty amides preferably having from 2 to 30 mol of ethylene oxide, polyglycerolated fatty amides containing on average 1 to 5, and in particular 1.5 to 4, glycerol groups; polyethoxylated fatty amines preferably having 2 to 30 mol of ethylene oxide; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, and amine oxides such as $(C_{10}-C_{14})$alkylamine oxides or N-acylaminopropylmorpholine oxides.

The amphoteric or Zwitterionic surfactants, can be, in particular, aliphatic secondary or tertiary amine derivatives in which the aliphatic radical is a linear or branched chain containing 8 to 18 carbon atoms and containing at least one water-solubilizing anionic group (for example carboxylate, sulfonate, sulfate, phosphate or phosphonate); mention may also be made of $(C_8-C_{20})$alkylbetaines, sulfobetaines, $(C_8-C_{20})$alkylamido$(C_1-C_6)$alkylbetaines or $(C_8-C_{20})$alkylamido$(C_1-C_6)$alkylsulfobetaines.

Among the amine derivatives, mention may be made of the products sold under the name Miranol, as described in U.S. Pat. Nos. 2,528,378 and 2,781,354 and classified in the CTFA dictionary, 3rd edition, 1982, under the names Amphocarboxyglycinates and Amphocarboxypropionates.

These compounds are classified in the CTFA dictionary, 5th edition, 1993, under the names Disodium Cocoamphodiacetate, Disodium Lauroamphodiacetate, Disodium Caprylamphodiacetate, Disodium Caprylloamphodiacetate, Disodium Cocoamphodipropionate, Disodium Lauroamphopropionate, Disodium Caprylamphodipropionate, Disodium Caprylloamphodipropionate, Lauroamphodipropionic acid and Cocoamphodipropionic acid.

By way of example, mention may be made of the cocoamphodiacetate sold under the trade name Miranol® C2M concentrate by the company Rhodia Chimie.

Among the cationic surfactants, mention may be made in particular of: salts of optionally polyoxyalkylenated primary, secondary or tertiary fatty amines; quaternary ammonium salts such as tetraalkylammonium, alkylamido-alkyltrialkylammonium, trialkylbenzylammonium, trialkylhydroxyalkylammonium or alkylpyridinium chlorides or bromides; imidazoline derivatives; or amine oxides of cationic nature.

When they are present in the composition in accordance with the invention, the surfactant(s) is (are) each generally present in an amount of between 0.01% and 40% by weight relative to the total weight of the composition, and preferably between 0.5% and 30% by weight relative to the total weight of the composition.

The thickening polymers that are useful in the context of the present invention include any water-soluble or water-dispersible polymer, which is synthetic or of natural origin, conventionally used in cosmetics.

As examples of synthetic polymers, mention may be made of polyvinylpyrrolidone, crosslinked polyacrylic acids, polyacrylamide, non-crosslinked poly-2-acrylamidopropanesulfonic acid such as, for example, the product sold under the name Simulgel EG® by the company SEPPIC, crosslinked poly-2-acrylamido-2-methylpropanesulfonic acid, poly-2-acrylamido-2-methylpropanesulfonic acid crosslinked and partially neutralized with aqueous ammonia, sold under the brand name Hostacerin AMPS® by the company Clariant, mixtures with a synergistic thickening effect of the non-crosslinked poly-2-acrylamido-2-methylpropanesulfonic acid with hydroxyalkylcellulose ethers or with polyethylene oxide) as described in U.S. Pat. No. 4,540,510, or mixtures with a synergistic thickening effect of a poly(meth)acrylamido$(C_1-C_4)$alkylsulfonic acid preferably crosslinked with a crosslinked copolymer of maleic anhydride and of a $(C_1-C_5)$ alkyl vinyl ether such as the mixture Hostacerin AMPS®/Stabileze QM® (from the company ISF) and as described in French patent application FR 0 014 416 from the Applicant.

The modified or unmodified thickening polymers of natural origin that may be used according to the present invention are preferably polymers comprising at least one sugar unit, namely: nonionic guar gums; biopolysaccharide gums of microbial origin such as scleroglucan gum or xanthan gum; gums derived from plant exudates, such as gum arabic, ghatti gum, karaya gum, gum tragacanth, carrageenan, agar and carob gum; pectins; alginates; starches; hydroxy$(C_1-C_6)$alkylcelluloses and carboxy$(C_1-C_6)$alkylcelluloses.

For the purposes of the present invention, the expression "sugar unit" denotes a monosaccharide portion (i.e. monosaccharide or oside or simple sugar) or an oligosaccharide portion (short chains formed from the linking of monosaccharide units, which may be different) or a polysaccharide portion [long chains consisting of monosaccharide units, which may be different, i.e. polyholosides or polyosides (homopolyosides or heteropolyosides)]. The saccharide units can also be substituted with alkyl, hydroxyalkyl, alkoxy, acyloxy or carboxyl radicals, or alkyl radicals containing from 1 to 4 carbon atoms.

The nonionic guar gums may be modified or unmodified. The unmodified guar gums are, for example, the products sold under the name Guargel® D/15 by the company Goodrich, Vidogum® GH 175 by the company Unipectine and under the names Meypro-Guar® 50 and Jaguar® C by the company Meyhall.

The modified nonionic guar gums are especially modified with $C_1-C_6$ hydroxyalkyl groups.

Among the hydroxyalkyl groups that may be mentioned, for example, are hydroxymethyl, hydroxyethyl, hydroxypropyl and hydroxybutyl groups.

These guar gums are well known in the state of the art and can be prepared, for example, by reacting the corresponding alkene oxides such as, for example, propylene oxides, with the guar gum so as to obtain a guar gum modified with hydroxypropyl groups.

The degree of hydroxyalkylation, which corresponds to the number of alkylene oxide molecules consumed by the number of free hydroxyl functions present on the guar gum, preferably ranges from 0.4 to 1.2.

Such nonionic guar gums optionally modified with hydroxyalkyl groups are sold, for example, under the trade names Jaguar® HP8, Jaguar® HP60 and Jaguar® HP120, Jaguar® DC 293 and Jaguar® HP 105 by the company Rhône-Poulenc (Meyhall) or under the name Galactasol® 4H4FD2 by the company Aqualon.

The biopolysaccharide gums of microbial origin, such as the scleroglucan or xanthan gums, the gums derived from plant exudates such as gum arabic, ghatti gum, karaya gum, gum tragacanth, carrageenan gum, agar gum and carob gum, the hydroxyalkylcelluloses and carboxymethylcelluloses, pectins, alginates and starches are well known to those skilled in the art and are described in particular in the book by Robert L. Davidson entitled "Handbook of Water soluble gums and resins" published by McGraw Hill Book Company (1980).

Among these gums, the scleroglucans are represented by the products sold under the name Actigum® CS by the company Sanofi Bio Industries and in particular Actigum® CS 11, and under the name Amigel® by the company Alban Muller International. Other scleroglucans, such as the one treated with glyoxal in French patent application FR 2 633 940, can also be used.

The xanthans are represented by the products sold under the names Keltrol®, Keltrol® T, Keltrol® TF, Keltrol® BT, Keltrol® RD and Keltrol® CG by the company Nutrasweet Kelco, or under the names Rhodicare® S and Rhodicare® H by the company Rhodia Chimie.

Among the starch derivatives that may be mentioned, for example, is the product sold under the name Primogel® by the company Avebe.

The hydroxy($C_1$-$C_6$)alkylcelluloses are more particularly hydroxyethylcelluloses, such as those sold under the names Cellosize® QP3L, Cellosize® QP4400H, Cellosize® QP30000H, Cellosize® HEC30000A and Cellosize® Polymer PCG10 by the company Amerchol, or Natrosol® 250HHR, Natrosol® 250MR, Natrosol® 250M, Natrosol® 250HHXR, Natrosol® 250HHX, Natrosol® 250HR and Natrosol® HX by the company Hercules, or Tylose® H1000 by the company Hoechst.

The hydroxy($C_1$-$C_6$)alkylcelluloses are also, more particularly, hydroxypropylcelluloses such as the products sold under the names Klucel® EF, Klucel® H, Klucel® LHF, Klucel® MF and Klucel® G by the company Aqualon.

Among the carboxy($C_1$-$C_6$)alkylcelluloses preferably used is carboxymethylcellulose, for which mention may be made of the products sold under the names Blanose® 7M8/SF, Blanose® Raffinée 7M, Blanose® 7LF, Blanose® 7MF, Blanose® 9M31F, Blanose® 12M31XP, Blanose® 12M31P, Blanose® 9M31XF, Blanose® 7H, Blanose® 7M31 and Blanose® 7H3SXF by the company Aqualon, or Aquasorb® A500 and Ambergum® 1221 by the company Hercules, or Cellogen® HP810A and Cellogen® HP6HS9 by the company Montello, or Primellose® by the company Avebe.

When they are present in the composition of the present invention, the water-soluble or water-dispersible thickening polymers are each generally present in an amount of less than or equal to 10% by weight and preferably less than equal to 5% by weight relative to the total weight of the said composition.

The associative polymers that are useful in the composition of the invention are water-soluble or water-dispersible polymers capable, in an aqueous medium, of reversibly associating together or with other molecules.

Their chemical structure comprises hydrophilic zones and hydrophobic zones characterized by at least one fatty chain.

The associative polymer(s) may be chosen without preference, alone or as mixtures, from anionic, amphoteric, nonionic and cationic associative polymers.

Among the anionic associative polymers that may be mentioned are the following polymers:

(I) those comprising at least one hydrophilic unit and at least one fatty-chain allyl ether unit, more particularly those whose hydrophilic unit consists of an ethylenic unsaturated anionic monomer.

Anionic associative polymers of this type are described and prepared, according to an emulsion polymerization process, in patent EP-0 216 479.

Among these anionic associative polymers that are particularly preferred according to the invention are polymers formed from 20% to 60% by weight of acrylic acid and/or of methacrylic acid, from 5% to 60% by weight of lower alkyl (meth)acrylates, from 2% to 50% by weight of fatty-chain allyl ether, and from 0 to 1% by weight of a crosslinking agent which is a well-known copolymerizable unsaturated polyethylenic monomer, for instance diallyl phthalate, allyl (meth)acrylate, divinylbenzene, (poly)ethylene glycol dimethacrylate or methylenebisacrylamide.

Among the latter polymers, those most particularly preferred are crosslinked terpolymers of methacrylic acid, of ethyl acrylate and of polyethylene glycol (10 EO) stearyl ether (Steareth-10), in particular those sold by the company Allied Colloids under the names Salcare SC 80® and Salcare SC 90®, which are aqueous 30% emulsions of a crosslinked terpolymer of methacrylic acid, of ethyl acrylate and of steareth-10 alkyl ether (40/50/10).

(II) those comprising at least one hydrophilic unit of unsaturated olefinic carboxylic acid type, and at least one hydrophobic unit of ($C_{10}$-$C_{30}$)alkyl ester of unsaturated carboxylic acid type.

Anionic polymers of this type are described and prepared, for example, according to U.S. Pat. Nos. 3,915,921 and 4,509,949.

Among anionic associative polymers of this type that will be used more particularly are those consisting of from 95% to 60% by weight of acrylic acid (hydrophilic unit), from 4% to 40% by weight of $C_{10}$-$C_{30}$ alkyl acrylate (hydrophobic unit) and from 0% to 6% by weight of crosslinking polymerizable monomer, or alternatively those consisting of from 98% to 96% by weight of acrylic acid (hydrophilic unit), from 1% to 4% by weight of $C_{10}$-$C_{30}$ alkyl acrylate (hydrophobic unit) and from 0.1% to 0.6% by weight of crosslinking polymerizable monomer such as those described above.

Among the said above polymers, those most particularly preferred according to the present invention are the products sold by the company Goodrich under the trade names Pemulen TR1®, Pemulen TR2® and Carbopol 1382®, and even more preferentially Pemulen TR1®, and the product sold by the company SEPPIC under the name Coatex SX®.

(III) maleic anhydride/$C_{30}$-$C_{38}$ α-olefin/alkyl maleate terpolymers, such as the product (maleic anhydride/$C_{30}$-

$C_{38}$ α-olefin/isopropyl maleate copolymer) sold under the name Performa V 1608® by the company Newphase Technologies.

(IV) acrylic terpolymers comprising:

(a) about 20% to 70% by weight of a carboxylic acid containing α,β-monoethylenic unsaturation, (b) about 20% to 80% by weight of a non-surfactant monomer containing α,β-monoethylenic unsaturation other than (a), (c) about 0.5% to 60% by weight of a nonionic monourethane which is the product of reaction of a monohydric surfactant with a monoisocyanate containing monoethylenic unsaturation, such as those described in patent application EP-A-0 173 109 and more particularly a methacrylic acid/methyl acrylate/behenyl dimethyl-meta-isopropenyl-benzylisocyanate ethoxylated (40 EO) terpolymer, as an aqueous 25% dispersion.

(V) copolymers comprising among their monomers a carboxylic acid containing α,β-monoethylenic unsaturation and an ester of a carboxylic acid containing α,β-monoethylenic unsaturation and of an oxyalkylenated fatty alcohol.

Preferentially, these compounds also comprise as monomer an ester of a carboxylic acid containing α,β-monoethylenic unsaturation and of a $C_1$-$C_4$ alcohol.

An example of a compound of this type which may be mentioned is Aculyn 22® sold by the company Rohm & Haas, which is a methacrylic acid/ethyl acrylate/stearyl methacrylate oxyalkylenated terpolymer.

(VI) amphiphilic polymers comprising at least one ethylenically unsaturated monomer containing a sulfonic group, in free form or partially or totally neutralized form and comprising at least one hydrophobic portion.

The expression "amphiphilic polymer" means any polymer comprising both a hydrophilic portion and a hydrophobic portion and especially a fatty chain.

The hydrophobic portion present in the polymers of the invention preferably contains from 6 to 50 carbon atoms, more preferably from 6 to 22 carbon atoms, even more preferably from 6 to 18 carbon atoms and more particularly from 12 to 18 carbon atoms.

Preferably, the polymers in accordance with the invention are partially or totally neutralized with a mineral base (sodium hydroxide, potassium hydroxide or aqueous ammonia) or an organic base such as mono-, di- or triethanolamine, an aminomethylpropanediol, N-methylglucamine, basic amino acids, for instance arginine and lysine, and mixtures of these compounds.

The amphiphilic polymers in accordance with the invention generally have a number-average molecular weight ranging from 1000 to 20 000 000 g/mol, preferably ranging from 20 000 to 5 000 000 and even more preferably from 100 000 to 1 500 000 g/mol.

The amphiphilic polymers according to the invention may or may not be crosslinked.

Crosslinked amphiphilic polymers are preferably chosen.

When they are crosslinked, the crosslinking agents may be chosen from polyolefinically unsaturated compounds commonly used for the crosslinking of polymers obtained by free-radical polymerization.

Mention may be made, for example, of divinylbenzene, diallyl ether, dipropylene glycol diallyl ether, polyglycol diallyl ethers, triethylene glycol divinyl ether, hydroquinone diallyl ether, ethylene glycol di(meth)acrylate or tetraethylene glycol di(meth)acrylate, trimethylolpropane triacrylate, methylenebisacrylamide, methylenebismethacrylamide, triallylamine, triallyl cyanurate, diallyl maleate, tetraallylethylenediamine, tetraallyloxyethane, trimethylolpropane diallyl ether, allyl (meth)acrylate, allylic ethers of alcohols of the sugar series, or other allyl or vinyl ethers of polyfunctional alcohols, and also allylic esters of phosphoric and/or vinylphosphonic acid derivatives, or mixtures of these compounds.

Methylenebisacrylamide, allyl methacrylate or trimethylolpropane triacrylate (TMPTA) will be used more particularly. The degree of crosslinking will generally range from 0.01 mol % to 10 mol % and more particularly from 0.2 mol % to 2 mol % relative to the polymer.

The ethylenically unsaturated monomers containing a sulfonic group are chosen especially from vinylsulfonic acid, styrenesulfonic acid, (meth)acrylamido($C_1$-$C_{22}$)alkylsulfonic acids, and N-($C_1$-$C_{22}$)alkyl(meth)acrylamido($C_1$-$C_{22}$) alkylsulfonic acids, for instance undecyl-acrylamidomethanesulfonic acid, and also partially or totally neutralized forms thereof.

(Meth)acrylamido($C_1$-$C_{22}$)alkylsulfonic acids such as, for example, acrylamidomethanesulfonic acid, acrylamidoethanesulfonic acid, acrylamidopropanesulfonic acid, 2-acrylamido-2-methylpropanesulfonic acid, methacrylamido-2-methylpropanesulfonic acid, 2-acrylamido-n-butanesulfonic acid, 2-acrylamido-2,4,4-trimethylpentanesulfonic acid, 2-methacrylamidododecylsulfonic acid or 2-acrylamido-2,6-dimethyl-3-heptanesulfonic acid, and also partially or totally neutralized forms thereof, will more preferably be used.

2-Acrylamido-2-methylpropanesulfonic acid (AMPS), and also partially or totally neutralized forms thereof, will more particularly be used.

The amphiphilic polymers in accordance with the invention may be chosen especially from random amphiphilic AMPS polymers modified by reaction with a $C_6$-$C_{22}$ n-monoalkylamine or di-n-alkylamine, and such as those described in patent application WO-A-00/31154 (forming an integral part of the content of the description). These polymers may also contain other ethylenically unsaturated hydrophilic monomers chosen, for example, from (meth)acrylic acids, β-substituted alkyl derivatives thereof or esters thereof obtained with monoalcohols or mono- or polyalkylene glycols, (meth)acrylamides, vinylpyrrolidone, maleic anhydride, itaconic acid or maleic acid, or mixtures of these compounds.

The preferred polymers of the invention are chosen from amphiphilic copolymers of AMPS and of at least one ethylenically unsaturated hydrophobic monomer comprising at least one hydrophobic portion containing from 6 to 50 carbon atoms, more preferably from 6 to 22 carbon atoms, even more preferably from 6 to 18 carbon atoms and more particularly 12 to 18 carbon atoms.

These same copolymers may also contain one or more ethylenically unsaturated monomers not comprising a fatty chain, such as (meth)acrylic acids, β-substituted alkyl derivatives thereof or esters thereof obtained with monoalcohols or mono- or polyalkylene glycols, (meth)acrylamides, vinylpyrrolidone, maleic anhydride, itaconic acid or maleic acid, or mixtures of these compounds.

These copolymers are described especially in patent application EP-A-750 899, U.S. Pat. No. 5,089,578 and in the following publications from Yotaro Morishima:

"Self-assembling amphiphilic polyelectrolytes and their nanostructures—Chinese Journal of Polymer Science Vol. 18, No. 40, (2000), 323-336";

"Micelle formation of random copolymers of sodium 2-(acrylamido)-2-methylpropanesulfonate and a nonionic surfactant macromonomer in water as studied by fluorescence and dynamic light scattering—Macromolecules 2000, Vol. 33, No. 10-3694-3704";

"Solution properties of micelle networks formed by nonionic moieties covalently bound to a polyelectrolyte: salt effects on rheological behavior—Langmuir, 2000, Vol. 16, No. 12, 5324-5332";

"Stimuli responsive amphiphilic copolymers of sodium 2-(acrylamido)-2-methylpropanesulfonate and associative macromonomers—Polym. Preprint, Div. Polym. Chem. 1999, 40(2), 220-221".

The ethylenically unsaturated hydrophobic monomers of these particular copolymers are preferably chosen from the acrylates or acrylamides of formula (I) below:

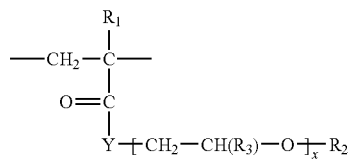

(I)

in which $R_1$ and $R_3$, which may be identical or different, denote a hydrogen atom or a linear or branched $C_1$-$C_6$ alkyl radical (preferably methyl); Y denotes O or NH; $R_2$ denotes a hydrophobic hydrocarbon-based radical containing at least from 6 to 50 carbon atoms, more preferably from 6 to 22 carbon atoms, even more preferably from 6 to 16 carbon atoms and more particularly from 12 to 18 carbon atoms; x denotes a number of moles of alkylene oxide and ranges from 0 to 100.

The radical $R_2$ is preferably chosen from linear $C_6$-$C_{18}$ alkyl radicals (for example n-hexyl, n-octyl, n-decyl, n-hexadecyl and n-dodecyl) and branched or cyclic $C_6$-$C_{18}$ alkyl radicals (for example cyclododecane ($C_{12}$) or adamantane ($C_{10}$)); $C_6$-$C_{18}$ alkylperfluoro radicals (for example the group of formula —$(CH_2)_2$—$(CF_2)_9$—$CF_3$); the cholesteryl radical ($C_{27}$) or a cholesterol ester residue, for instance the cholesteryl oxyhexanoate group; aromatic polycyclic groups, for instance naphthalene or pyrene. Among these radicals, the ones that are more particularly preferred are linear alkyl radicals and more particularly the n-dodecyl radical.

According to one particularly preferred form of the invention, the monomer of formula (I) comprises at least one alkylene oxide unit ($x \geqq 1$) and preferably a polyoxyalkylenated chain. The polyoxyalkylenated chain preferably consists of ethylene oxide units and/or of propylene oxide units and even more particularly consists of ethylene oxide units. The number of oxyalkylene units generally ranges from 3 to 100, more preferably from 3 to 50 and even more preferably from 7 to 25.

Among these polymers, mention may be made of:
crosslinked or non-crosslinked, neutralized or non-neutralized copolymers comprising from 15% to 60% by weight of AMPS units and from 40% to 85% by weight of ($C_8$-$C_{16}$)alkyl(meth)acrylamide units or of ($C_8$-$C_{16}$) alkyl (meth)acrylate units relative to the polymer, such as those described in patent application EP-A-750 899;
terpolymers comprising from 10 mol % to 90 mol % of acrylamide units, from 0.1 mol % to 10 mol % of AMPS units and from 5 mol % to 80 mol % of n-($C_6$-$C_{18}$) alkylacrylamide units, such as those described in U.S. Pat. No. 5,089,578.

Mention may also be made of copolymers of totally neutralized AMPS and of dodecyl methacrylate, and also crosslinked and non-crosslinked copolymers of AMPS and of n-dodecylmethacrylamide, such as those described in the Morishima articles mentioned above.

Mention will be made more particularly of the copolymers consisting of 2-acrylamido-2-methylpropanesulfonic acid (AMPS) units of formula (II) below:

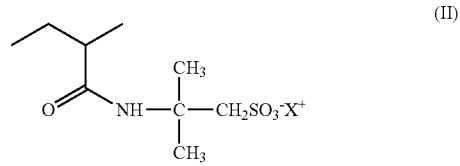

(II)

in which $X^+$ is a proton, an alkali metal cation, an alkaline-earth metal cation or the ammonium ion, and of units of formula (III) below:

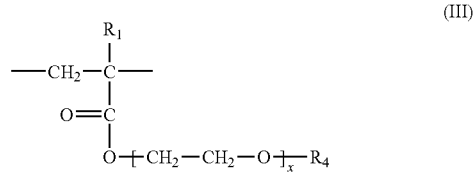

(III)

in which x denotes an integer ranging from 3 to 100, preferably from 5 to 80 and more preferably from 7 to 25; $R_1$ has the same meaning as that given above in formula (I) and $R_4$ denotes a linear or branched $C_6$-$C_{22}$ and more preferably $C_{10}$-$C_{22}$ alkyl.

The polymers that are particularly preferred are those for which x=25, $R_1$ denotes methyl and $R_4$ represents n-dodecyl; they are described in the Morishima articles mentioned above.

The polymers for which $X^+$ denotes sodium or ammonium are more particularly preferred.

The preferred amphiphilic polymers in accordance with the invention may be obtained according to the standard free-radical polymerization processes in the presence of one or more initiators such as, for example, azobisisobutyronitrile (AIBN), azobisdimethylvaleronitrile, ABAH (2,2-azobis[2-amidinopropane] hydrochloride), organic peroxides such as dilauryl peroxide, benzoyl peroxide, tert-butyl hydroperoxide, etc., mineral peroxide compounds such as potassium persulfate or ammonium persulfate, or $H_2O_2$ optionally in the presence of reducing agents.

The amphiphilic polymers are obtained especially by free-radical polymerization in tert-butanol medium in which they precipitate.

Using precipitation polymerization in tert-butanol, it is possible to obtain a size distribution of the polymer particles that is particularly favourable for its uses.

The size distribution of the polymer particles may be determined, for example, by laser diffraction or image analysis.

An advantageous distribution for this type of polymer, determined by image analysis, is as follows: 60.2% less than 423 microns, 52.0% less than 212 microns, 26.6% less than 106 microns, 2.6% less than 45 microns and 26.6% greater than 850 microns.

The reaction may be performed at a temperature of between 0 and 150° C., preferably between 10 and 100° C., either at atmospheric pressure or under reduced pressure. It may also be performed under inert atmosphere, and preferably under nitrogen.

According to this process 2-acrylamido-2-methylpropanesulfonic acid (AMPS) or a sodium or ammonium salt thereof was especially polymerized with a (meth)acrylic acid ester and

- a $C_{10}$-$C_{18}$ alcohol oxyethylenated with 8 mol of ethylene oxide (Genapol® C-080 from the company Hoechst/Clariant),
- a $C_{11}$ oxo alcohol oxyethylenated with 8 mol of ethylene oxide (Genapol® UD-080 from the company Hoechst/Clariant),
- a $C_{11}$ oxo alcohol oxyethylenated with 7 mol of ethylene oxide (Genapol® UD-070 from the company Hoechst/Clariant),
- a $C_{12}$-$C_{14}$ alcohol oxyethylenated with 7 mol of ethylene oxide (Genapol® LA-070 from the company Hoechst/Clariant),
- a $C_{12}$-$C_{14}$ alcohol oxyethylenated with 9 mol of ethylene oxide (Genapol® LA-090 from the company Hoechst/Clariant),
- a $C_{12}$-$C_{14}$ alcohol oxyethylenated with 11 mol of ethylene oxide (Genapol®) LA-110 from the company Hoechst/Clariant),
- a $C_{16}$-$C_{18}$ alcohol oxyethylenated with 8 mol of ethylene oxide (Genapol® T-080 from the company Hoechst/Clariant),
- a $C_{16}$-$C_{18}$ alcohol oxyethylenated with 15 mol of ethylene oxide (Genapol® T-150 from the company Hoechst/Clariant),
- a $C_{16}$-$C_{18}$ alcohol oxyethylenated with 11 mol of ethylene oxide (Genapol® T-110 from the company Hoechst/Clariant),
- a $C_{16}$-$C_{18}$ alcohol oxyethylenated with 20 mol of ethylene oxide (Genapol® T-200 from the company Hoechst/Clariant),
- a $C_{16}$-$C_{18}$ alcohol oxyethylenated with 25 mol of ethylene oxide (Genapol® T-250 from the company Hoechst/Clariant),
- a $C_{18}$-$C_{22}$ alcohol oxyethylenated with 25 mol of ethylene oxide and/or a $C_{16}$-$C_{18}$ iso alcohol oxyethylenated with 25 mol of ethylene oxide.

The molar % concentration of the units of formula (II) and of the units of formula (III) in the polymers according to the invention will vary as a function of the desired cosmetic use and of the desired rheological properties of the formulation. It may range between 0.1 mol % and 99.9 mol %.

Preferably, for the most hydrophobic polymers, the molar proportion of units of formula (I) or (III) ranges from 50.1% to 99.9%, more particularly from 70% to 95% and even more particularly from 80% to 90%.

Preferably, for the sparingly hydrophobic polymers, the molar proportion of units of formula (I) or (III) ranges from 0.1% to 50%, more particularly from 5% to 25% and even more particularly from 10% to 20%.

The monomer distribution in the polymers of the invention may be, for example, alternating, block (including multiblock) or random.

According to the invention, it is preferable for the polymers to contain heat-sensitive pendant chains and for the aqueous solution thereof to have a viscosity that, beyond a certain threshold temperature, increases or remains virtually constant as the temperature increases.

Even more particularly, the preferred polymers are those whose aqueous solution has a viscosity that is low below a first threshold temperature and that, above this first threshold temperature, increases to a maximum as the temperature increases, and that, above a second threshold temperature, decreases again as the temperature increases. From this perspective, it is preferable for the viscosity of the polymer solutions below the first threshold temperature to be from 5% to 50%, in particular from 10% to 30% of the maximum viscosity at the second threshold temperature.

These polymers preferably lead in water to a phenomenon of demixing by heating, reflected by curves showing, as a function of the temperature and the concentration, a minimum known as the LCST (Lower Critical Solution Temperature).

The viscosities (measured at 25° C. using a Brookfield viscometer, needle No. 7) of the aqueous 1% solutions preferably range from 20 000 mPa·s to 100 000 mPa·s and more particularly from 60 000 mPa·s to 70 000 mPa·s.

Cationic associative polymers that may be mentioned include the following polymers:

(I) the cationic associative polyurethanes whose family has been described in French patent application FR 2 811 993.

The number-average molecular mass of the cationic associative polyurethanes is preferably between 400 and 500 000, in particular between 1000 and 400 000 and ideally between 1000 and 300 000.

The expression "hydrophobic group" means a radical or polymer containing a saturated or unsaturated, linear or branched hydrocarbon-based chain, which may contain one or more hetero atoms such as P, O, N or S, or a radical containing a perfluoro or silicone chain. When the hydrophobic group denotes a hydrocarbon-based radical, it comprises at least 10 carbon atoms, preferably from 10 to 30 carbon atoms, in particular from 12 to 30 carbon atoms and more preferably from 18 to 30 carbon atoms.

Preferentially, the hydrocarbon-based group is derived from a monofunctional compound.

By way of example, the hydrophobic group may be derived from a fatty alcohol such as stearyl alcohol, dodecyl alcohol or decyl alcohol. It may also denote a hydrocarbon-based polymer, for instance polybutadiene.

(II) quaternized cellulose derivatives and polyacrylates containing non-cyclic amine side groups.

The quaternized cellulose derivatives are, in particular:

quaternized celluloses modified with groups comprising at least one fatty chain, such as alkyl, arylalkyl or alkylaryl groups containing at least 8 carbon atoms, or mixtures thereof, quaternized hydroxyethylcelluloses modified with groups comprising at least one fatty chain, such as alkyl, arylalkyl or alkylaryl groups containing at least 8 carbon atoms, or mixtures thereof.

The alkyl radicals borne by the above quaternized celluloses or hydroxyethylcelluloses preferably contain from 8 to 30 carbon atoms. The aryl radicals preferably denote phenyl, benzyl, naphthyl or anthryl groups.

Examples of quaternized alkylhydroxyethylcelluloses containing $C_8$-$C_{30}$ fatty chains that may be mentioned include the products Quatrisoft LM 200®, Quatrisoft LM-X 529-18-A®, Quatrisoft LM-X 529-18B® ($C_{12}$ alkyl) and Quatrisoft LM-X 529-8® ($C_{18}$ alkyl) sold by the company Amerchol, and the products Crodacel QM®, Crodacel QL® ($C_{12}$ alkyl) and Crodacel QS® ($C_{18}$ alkyl) sold by the company Croda.

The amphoteric associative polymers are preferably chosen from those comprising at least one non-cyclic cationic unit. More particularly, the ones that are preferred are those prepared from or comprising 1 to 20 mol %, preferably 1.5 to 15 mol % and even more particularly 1.5 to 6 mol % of fatty-chain monomer relative to the total number of moles of monomers.

The weight-average molecular weights of the amphoteric associative polymers that are useful in the context of the invention may range from 500 to 50 000 000 and are preferably between 10 000 and 5 000 000.

The amphoteric associative polymers that are useful in the context of the invention may also contain other monomers such as nonionic monomers and in particular such as $C_1$-$C_4$ alkyl acrylates or methacrylates.

Amphoteric associative polymers according to the invention are described and prepared, for example, in patent application WO 98/44012.

Among the amphoteric associative polymers that are useful in the context of the invention, the ones that are preferred are acrylic acid/(meth)acrylamidopropyltrimethylammonium chloride/stearyl methacrylate terpolymers.

According to the invention, the nonionic associative polymers are preferably chosen from:
(1) celluloses modified with groups comprising at least one fatty chain; examples that may be mentioned include:
hydroxyethylcelluloses modified with groups comprising at least one fatty chain, such as alkyl, arylalkyl or alkylaryl groups, or mixtures thereof, and in which the alkyl groups are preferably $C_8$-$C_{22}$, for instance the product Natrosol Plus Grade 330 CS® ($C_{16}$ alkyls) sold by the company Aqualon, or the product Bermocoll EHM 100® sold by the company Berol Nobel,
those modified with alkylphenyl polyalkylene glycol ether groups, such as the product Amercell Polymer HM-15000 (nonylphenyl polyethylene glycol (15) ether) sold by the company Amerchol.
(2) hydroxypropyl guars modified with groups comprising at least one fatty chain, such as the product Esaflor HM 22® ($C_{22}$ alkyl chain) sold by the company Lamberti, and the products RE210-18® ($C_{14}$ alkyl chain) and RE205-1® ($C_{20}$ alkyl chain) sold by the company Rhone-Poulenc.
(3) copolymers of vinylpyrrolidone and of fatty-chain hydrophobic monomers of which examples that may be mentioned include:
the products Antaron V216® or Ganex V216® (vinylpyrrolidone/hexadecene copolymer) sold by the company I.S.P.
the products Antaron V220® or Ganex V220® (vinylpyrrolidone/eicosene copolymer) sold by the company I.S.P.
(4) copolymers of $C_1$-$C_6$ alkyl methacrylates or acrylates and of amphiphilic monomers comprising at least one fatty chain, such as, for example, the oxyethylenated methyl acrylate/stearyl acrylate copolymer sold by the company Goldschmidt under the name Antil 208®.
(5) copolymers of hydrophilic methacrylates or acrylates and of hydrophobic monomers comprising at least one fatty chain, such as, for example, the polyethylene glycol methacrylate/lauryl methacrylate copolymer.
(6) polyurethane polyethers comprising in their chain both hydrophilic blocks usually of polyoxyethylenated nature and hydrophobic blocks which may be aliphatic sequences alone and/or cycloaliphatic and/or aromatic sequences.
(7) polymers with an aminoplast ether skeleton containing at least one fatty chain, such as the Pure Thix® compounds sold by the company Sud-Chemie.

Preferably, the polyurethane polyethers comprise at least two hydrocarbon-based lipophilic chains containing from 6 to 30 carbon atoms, separated by a hydrophilic block, the hydrocarbon-based chains possibly being pendent chains, or chains at the end of the hydrophilic block. In particular, it is possible for one or more pendent chains to be included. In addition, the polymer may comprise a hydrocarbon-based chain at one end or at both ends of a hydrophilic block.

The polyurethane polyethers may be multiblock, in particular in triblock form. Hydrophobic blocks may be at each end of the chain (for example: triblock copolymer with a hydrophilic central block) or distributed both at the ends and in the chain (for example: multiblock copolymer). These same polymers may also be graft polymers or starburst polymers.

The nonionic fatty-chain polyurethane polyethers may be triblock copolymers in which the hydrophilic block is a polyoxyethylenated chain comprising from 50 to 1000 oxyethylene groups. The nonionic polyurethane polyethers comprise a urethane linkage between the hydrophilic blocks, whence arises the name.

By extension, also included among the nonionic fatty-chain polyurethane polyethers are those in which the hydrophilic blocks are linked to the lipophilic blocks via other chemical bonds.

As examples of nonionic fatty-chain polyurethane polyethers that may be used in the invention, it is also possible to use Rheolate 205® containing a urea function, sold by the company Rheox, or Rheolate® 208, 204 or 212, and also Acrysol RM 184®.

Mention may also be made of the product Elfacos T210® containing a $C_{12-14}$ alkyl chain, and the product Elfacos T212® containing a $C_{18}$ alkyl chain, from Akzo.

The product DW 1206B® from Rohm & Haas containing a $C_{20}$ alkyl chain and a urethane linkage, sold at a solids content of 20% in water, may also be used.

It is also possible to use solutions or dispersions of these polymers, especially in water or in aqueous-alcoholic medium. Examples of such polymers that may be mentioned are Rheolate® 255, Rheolate® 278 and Rheolate® 244 sold by the company Rheox. The products DW 1206F and DW 1206J sold by the company Rohm & Haas may also be used.

The polyurethane polyethers that may be used according to the invention are in particular those described in the article by G. Fonnum, J. Bakke and F k. Hansen—Colloid Polym. Sci 271, 380.389 (1993).

It is even more particularly preferred, in the context of the invention, to use a polyurethane polyether that may be obtained by polycondensation of at least three compounds comprising (i) at least one polyethylene glycol comprising from 150 to 180 mol of ethylene oxide, (ii) stearyl alcohol or decyl alcohol, and (iii) at least one diisocyanate.

Such polyurethane polyethers are sold especially by the company Rohm & Haas under the names Aculyn 46® and Aculyn 44®. Aculyn 46® is a polycondensate of polyethylene glycol containing 150 or 180 mol of ethylene oxide, of stearyl alcohol and of methylenebis(4-cyclohexyl isocyanate) (SMDI), at 15% by weight in a matrix of maltodextrin (4%) and water (81%); Aculyn 44® is a polycondensate of polyethylene glycol containing 150 or 180 mol of ethylene oxide, of decyl alcohol and of methylenebis(4-cyclohexylisocyanate) (SMDI), at 35% by weight in a mixture of propylene glycol (39%) and water (26%).

When they are present in the composition in accordance with the invention, the associative polymer(s) is (are) each generally present in an amount of less than or equal to 10% by weight and preferably less than or equal to 5% by weight relative to the total weight of the composition.

The composition in accordance with the present invention may also comprise at least one alkaline agent.

The alkaline agent(s) may be chosen from organic amines, aqueous ammonia and silicates.

When the composition in accordance with the invention comprises one or more alkaline agents, they are generally present in an amount of between 0.01% and 40% by weight and preferably between 0.1% and 30% by weight relative to the total weight of the composition.

The composition in accordance with the present invention may also comprise at least one persalt.

The persalt(s) may be chosen from ammonium or alkali metal perborates, percarbonates and persulfates.

When the composition in accordance with the invention comprises one or more persalts, they are generally present in an amount of between 10% and 70% by weight and preferably between 20% and 60% by weight relative to the total weight of the composition.

The composition in accordance with the present invention may also comprise at least one direct dye and/or at least one oxidation dye precursor.

The direct dye(s) may be chosen from the direct dyes conventionally used in direct dyeing. By way of example, these direct dyes are chosen from nitrobenzene dyes, azo direct dyes, methine direct dyes, quinone direct dyes, azine direct dyes, triarylmethane direct dyes, indoamine direct dyes and natural direct dyes. These direct dyes may be of nonionic, anionic or cationic nature.

Among the benzenic direct dyes, mention may be made of 1,4-diamino-2-nitrobenzene, 1-amino-2-nitro-4-($\beta$-hydroxyethylamino)benzene, 1-amino-2-nitro-4-bis($\beta$-hydroxyethyl)aminobenzene, 1,4-bis($\beta$-hydroxyethylamino)-2-nitrobenzene, 1-$\beta$-hydroxyethylamino-2-nitro-4-bis($\beta$-hydroxyethylamino)benzene, 1-$\beta$-hydroxyethylamino-2-nitro-4-aminobenzene, 1-p-hydroxyethylamino-2-nitro-4-(ethyl)($\beta$-hydroxyethyl)aminobenzene, 1-amino-3-methyl-4-$\beta$-hydroxyethylamino-6-nitrobenzene, 1-amino-2-nitro-4-$\beta$-hydroxyethylamino-5-chlorobenzene, 1,2-diamino-4-nitrobenzene, 1-amino-2-$\beta$-hydroxyethylamino-5-nitrobenzene, 1,2-bis($\beta$-hydroxyethylamino)-4-nitrobenzene, 1-amino-2-[tris(hydroxymethyl)methylamino]-5-nitrobenzene, 1-hydroxy-2-amino-5-nitrobenzene, 1-hydroxy-2-amino-4-nitrobenzene, 1-hydroxy-3-nitro-4-aminobenzene, 1-hydroxy-2-amino-4,6-dinitrobenzene, 1-$\beta$-hydroxyethyloxy-2-$\beta$-hydroxyethylamino-5-nitrobenzene, 1-methoxy-2-$\beta$-hydroxyethylamino-5-nitrobenzene, 1-$\beta$-hydroxyethyloxy-3-methylamino-4-nitrobenzene, 1-$\beta$,$\gamma$-dihydroxypropyloxy-3-methylamino-4-nitrobenzene, 1-$\beta$-hydroxyethylamino-4-$\beta$,$\gamma$-dihydroxypropyloxy-2-nitrobenzene, 1-$\beta$,$\gamma$-dihydroxypropylamino-4-trifluoromethyl-2-nitrobenzene, 1-$\beta$-hydroxyethylamino-4-trifluoromethyl-2-nitrobenzene, 1-$\beta$-hydroxyethylamino-3-methyl-2-nitrobenzene, 1-$\beta$-aminoethylamino-5-methoxy-2-nitrobenzene, 1-hydroxy-2-chloro-6-ethylamino-4-nitrobenzene, 1-hydroxy-2-chloro-6-amino-4-nitrobenzene, 1-hydroxy-6-[bis($\beta$-hydroxyethyl)amino]-3-nitrobenzene, 1-$\beta$-hydroxyethylamino-2-nitrobenzene and 1-hydroxy-4-$\beta$-hydroxyethylamino-3-nitrobenzene.

Among the azo direct dyes that may be mentioned are the cationic azo dyes described in patent applications WO 95/15144, WO 95/01772 and EP 0 714 954, the content of which forms an integral part of the invention.

Among these compounds, mention may be made most particularly of 1,3-dimethyl-2-[[4-(dimethylamino)phenyl]azo]-1H-imidazolium chloride, 1,3-dimethyl-2-[(4-aminophenyl)azo]-1H-imidazolium chloride and 1-methyl-4-[(methylphenylhydrazono)methyl]pyridinium methyl sulfate.

Among the azo direct dyes that may also be mentioned are the following dyes described in the Color Index International 3rd edition: Disperse Red 17; Acid Yellow 9; Acid Black 1; Basic Red 22; Basic Red 76; Basic Yellow 57; Basic Brown 16; Acid Yellow 36; Acid Orange 7; Acid Red 33; Acid Red 35; Basic Brown 17; Acid Yellow 23; Acid Orange 24; Disperse Black 9.

Mention may also be made of 1-(4'-aminodiphenylazo)-2-methyl-4-[bis($\beta$-hydroxyethyl)amino]benzene and 4-hydroxy-3-(2-methoxyphenylazo)-1-naphthalenesulfonic acid.

Among the quinone direct dyes that may be mentioned are the following dyes: Disperse Red 15; Solvent Violet 13; Acid Violet 43; Disperse Violet 1; Disperse Violet 4; Disperse Blue 1; Disperse Violet 8; Disperse Blue 3; Disperse Red 11; Acid Blue 62; Disperse Blue 7; Basic Blue 22; Disperse Violet 15; Basic Blue 99, and also the following compounds: 1-N-methylmorpholiniumpropylamino-4-hydroxyanthraquinone, 1-aminopropylamino-4-methylaminoanthraquinone, 1-aminopropylaminoanthraquinone, 5-$\beta$-hydroxyethyl-1,4-diaminoanthraquinone, 2-aminoethylaminoanthraquinone and 1,4-bis($\beta$,$\gamma$-dihydroxy-propylamino)anthraquinone.

Among the azine dyes that may be mentioned are the following compounds: Basic Blue 17 and Basic Red 2.

Among the triarylmethane dyes, mention may be made of the following compounds: Basic Green 1; Acid Blue 9; Basic Violet 3; Basic Violet 14; Basic Blue 7; Acid Violet 49; Basic Blue 26; Acid Blue 7.

Among the indoamine dyes, mention may be made of the following compounds: 2-$\beta$-hydroxyethylamino-5-[bis($\beta$-4'-hydroxyethyl)amino]anilino-1,4-benzoquinone, 2-$\beta$-hydroxyethylamino-5-(2'-methoxy-4'-amino)anilino-1,4-benzoquinone, 3-N-(2'-chloro-4'-hydroxy)phenylacetyl-amino-6-methoxy-1,4-benzoquinoneimine, 3-N-(3'-chloro-4'-methylamino)phenylureido-6-methyl-1,4-benzoquinoneimine and 3-[4'-N-(ethylcarbamylmethyl)amino]phenylureido-6-methyl-1,4-benzoquinoneimine.

Among the natural direct dyes that may be used according to the invention, mention may be made of lawsone, juglone, alizarin, purpurin, carminic acid, kermesic acid, purpurogallin, protocatechaldehyde, indigo, isatin, curcumin, spinulosin and apigenidin. Extracts or decoctions containing these natural dyes may also be used, and especially henna-based poultices or extracts.

When the composition in accordance with the invention comprises one or more direct dyes, they are generally present in an amount of between 0.001% and 20% by weight approximately, and even more preferentially between 0.005% and 10% by weight approximately relative to the total weight of the composition.

The oxidation dye precursors may be chosen from the oxidation bases and couplers conventionally used in the field of dyeing.

Examples of oxidation bases that may be mentioned include para-phenylenediamines, double bases, para-aminophenols, ortho-aminophenols and heterocyclic bases, and the addition salts thereof.

Among the para-phenylenediamines that may be mentioned, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-p-hydroxyethylamino-5-aminotoluene and 3-hydroxy-1-(4'-aminophenyl)pyrrolidine, and the addition salts thereof with an acid.

Among the para-phenylenediamines mentioned above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, are particularly preferred.

Among the double bases that may be mentioned, for example, are bis(phenyl)alkylenediamines and para-aminophenols.

Among the bis(phenyl)alkylenediamines that may be mentioned, for example, are N,N'-bis(β-hydroxyethyl)N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof with an acid.

Among the para-aminophenols that may be mentioned, for example, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof with an acid.

Among the heterocyclic bases that may be mentioned, for example, are pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the addition salts thereof with an acid.

Other pyridine oxidation bases that are useful in the present invention are the 3-aminopyrazolo[1,5-a]-pyridine oxidation bases or addition salts thereof described, for example, in patent application FR 2 801 308. Examples that may be mentioned include pyrazolo[1,5-a]pyrid-3-ylamine, 2-acetylaminopyrazolo-[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]-pyridine, pyrazolo[1,5-a]pyridine-3,7-diamine, 7-morpholin-4-ylpyrazolo[1,5-a]pyrid-3-ylamine, pyrazolo-[1,5-a]pyridine-3,5-diamine, 5-morpholin-4-ylpyrazolo-[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]-ethanol, 3-aminopyrazolo[1,5-a]pyridin-5-ol, 3-aminopyrazolo[1,5-a]pyridin-4-ol, 3-aminopyrazolo[1,5-a]-pyridin-6-ol and 3-aminopyrazolo[1,5-a]pyridin-7-ol, and the addition salts thereof with an acid or with a base.

Among the pyrimidine derivatives that may be mentioned are the compounds described, for example, in patents DE 2 359 399; JP 88-169 571; JP 05-63124; EP 0 770 375 or patent application WO 96/15765, for instance 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in patent application FR-A-2 750 048, and among which mention may be made of pyrazolo[1,5-a]-pyrimidine-3,7-diamine, 2,5-dimethylpyrazolo[1,5-a]-pyrimidine-3,7-diamine, pyrazolo[1,5-a]pyrimidine-3,5-diamine, 2,7-dimethylpyrazolo[1,5-a]pyrimidine-3,5-diamine, 3-aminopyrazolo[1,5-a]pyrimidin-7-ol, 3-aminopyrazolo[1,5-a]pyrimidin-5-ol, 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,-N7,N7-tetramethylpyrazolo[1,5-a]pyrimidine-3,7-diamine and 3-amino-5-methyl-7-imidazolylpropylaminopyrazolo[1,5-a]pyrimidine, and the addition salts thereof with an acid, and the tautomeric forms thereof, when a tautomeric equilibrium exists.

Among the pyrazole derivatives that may be mentioned are the compounds described in patents DE 3 843 892 and DE 4 133 957, and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3- hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof with an acid.

When the composition in accordance with the invention comprises one or more oxidation bases, they are generally present in an amount of between 0.001% and 10% by weight approximately and preferably between 0.005% and 6% by weight approximately relative to the total weight of the composition.

Examples of couplers that may be mentioned include meta-phenylenediamines, meta-aminophenols, meta-diphenols, naphthalene-based couplers and heterocyclic couplers, and the addition salts thereof.

Examples that may be mentioned include 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene and 2,6-bis(β-hydroxyethylamino)toluene, and the addition salts thereof with an acid.

When the composition in accordance with the invention comprises one or more couplers, they are generally present in an amount of between 0.001% and 10% by weight approximately and preferably between 0.005% and 6% by weight approximately relative to the total weight of the composition.

In general, the addition salts of the oxidation bases and couplers that may be used in the context of the invention are especially chosen from the addition salts with an acid such as the hydrochlorides, hydrobromides, sulfates, citrates, succinates, tartrates, lactates, tosylates, benzenesulfonates, phosphates and acetates, and the addition salts with a base, such as sodium hydroxide, potassium hydroxide, ammonia, amines or alkanolamines.

The cosmetically acceptable medium generally consists of water or of a mixture of water and of at least one organic solvent to dissolve the compounds that are not sufficiently water-soluble. Examples of organic solvents that may be mentioned include $C_1$-$C_4$ lower alkanols, such as ethanol and isopropanol; glycerol; glycols and glycol ethers, for instance 2-butoxyethanol, propylene glycol and propylene glycol monomethyl ether, and also aromatic alcohols, for instance benzyl alcohol or phenoxyethanol, similar products and mixtures thereof.

The solvents may be present in proportions preferably of between 1% and 40% by weight and even more preferentially between 5% and 30% by weight approximately relative to the total weight of the dye composition.

The composition in accordance with the present invention may also contain additives conventionally used in oxidizing compositions, in particular water-soluble or water-insoluble conditioning polymers, chelating agents, for instance ethylenediaminetetraacetic acid (EDTA) or pentasodium pentetate (CTFA name), and also hydrogen peroxide stabilizers such as, especially, sodium pyrophosphate, sodium stannate and sodium salicylate.

The content of additive(s) generally represents 0.001% to 20% by weight relative to the total weight of the compositions.

Needless to say, a person skilled in the art will take care to select the optional additional additive(s) mentioned above, such that the advantageous properties intrinsically associated with the anhydrous composition in accordance with the invention or the ready-to-use composition in accordance with the invention are not, or are not substantially, adversely affected by the envisaged addition(s).

The composition in accordance with the present invention may be in various forms, such as in the form of emulsions, creams or gels, or in any other suitable cosmetic form.

The bleaching process in accordance with the present invention consists in applying to the keratin fibres a composition in accordance with the invention as defined above.

When the composition in accordance with the invention comprises at least one alkaline agent and/or at least one persalt and/or at least one dye precursor and/or at least one direct dye as defined above, it may be obtained by mixing at least two compositions, one of these compositions being an aqueous composition comprising hydrogen peroxide and at least 20% by volume of inert particles as defined above. The alkaline agent(s) and/or the persalt(s) and/or the dye precursor(s) and/or the dye(s) are then distributed throughout the mixed compositions.

When the composition in accordance with the invention comprises at least one direct dye and/or at least one oxidation dye precursor, lightening dyeing is performed, i.e. bleaching and dyeing of the keratin fibres are simultaneously obtained.

According to one particular embodiment of the invention, the composition applied to the keratin fibres comprises at least one alkaline agent as defined above. It may then be obtained by mixing an aqueous composition comprising hydrogen peroxide and at least 20% by volume of inert particles as defined above and an aqueous composition comprising the alkaline agent(s).

According to another particular embodiment of the invention, the composition applied to the keratin fibres comprises at least one alkaline agent and at least one persalt as defined above. It may then be obtained by mixing an aqueous composition comprising hydrogen peroxide and at least 20% by volume of inert particles as defined above, an anhydrous composition comprising the persalt(s) and an aqueous composition comprising the alkaline agent(s). It may also be obtained by mixing an aqueous composition comprising hydrogen peroxide and at least 20% by volume of inert particles as defined above and an anhydrous composition comprising the persalt(s) and the alkaline agent(s).

According to another particular embodiment of the invention, the composition applied to the keratin fibres comprises at least one direct dye as defined above. It may then be obtained by mixing an aqueous composition comprising hydrogen peroxide and at least 20% by volume of inert particles as defined above and an aqueous composition comprising the direct dye(s).

According to another particular embodiment of the invention, the composition applied to the keratin fibres comprises at least one alkaline agent and at least one direct dye and/or at least one oxidation dye precursor as defined above. It may then be obtained by mixing an aqueous composition comprising hydrogen peroxide and at least 20% by volume of inert particles as defined above and an aqueous composition comprising the alkaline agent(s) and the direct dye(s) and/or the oxidation dye precursor(s). It may also be obtained by mixing an aqueous composition comprising hydrogen peroxide and at least 20% by volume of inert particles as defined above, an aqueous composition comprising the alkaline agent(s) and an aqueous composition comprising the direct dye(s) and/or the oxidation dye precursor(s).

According to another particular embodiment of the invention, the composition applied to the keratin fibres comprises at least one alkaline agent, at least one persalt and at least one direct dye as defined above. It may then be obtained by mixing an aqueous composition comprising hydrogen peroxide and at least 20% by volume of inert particles as defined above, an anhydrous composition comprising the persalt(s) and the alkaline agent(s) and an aqueous composition comprising the direct dye(s). It may also be obtained by mixing an aqueous composition comprising hydrogen peroxide and at least 20% by volume of inert particles as defined above, an anhydrous composition comprising the persalt(s), an aqueous composition comprising the alkaline agent(s) and an aqueous composition comprising the direct dye(s).

The compositions comprising the persalt(s) are anhydrous. They may also comprise additives that are common in the field, in particular water-soluble thickening polymers, fillers such as clays or amorphous silica, binders such as vinylpyrrolidone, lubricants, for instance polyol stearates or alkali metal or alkaline-earth metal stearates, and also oxygen-release controllers such as magnesium carbonate or oxide, colouring agents or matting agents, for instance titanium oxides, or alternatively anionic, nonionic, cationic or amphoteric surfactants, or vitamins.

By way of illustration, the content of additive(s) represents 0.01% to 40% by weight and preferably from 0.1% to 30% by weight relative to the total weight of the compositions.

The anhydrous compositions may be in the form of powder or paste. When they are in the form of paste, they also comprise an organic inert liquid chosen from the polydecenes of formula $C_{10n}H_{[(20n)+2]}$ in which n ranges from 3 to 9 and preferably from 3 to 7, esters of fatty alcohols or of fatty acids, $C_{12}$-$C_{24}$ fatty acid esters or diesters of sugars, cyclic ethers or cyclic esters, silicone oils, mineral oils or plant oils.

The other compositions are aqueous. The cosmetically acceptable medium of these compositions generally consists of water or of a mixture of water and of at least one organic solvent to dissolve the compounds that are not sufficiently water-soluble. Examples of organic solvents that may be mentioned include $C_1$-$C_4$ lower alkanols, such as ethanol and isopropanol; glycerol; glycols and glycol ethers, for instance 2-butoxyethanol, propylene glycol and propylene glycol monomethyl ether, and also aromatic alcohols, for instance benzyl alcohol or phenoxyethanol, similar products and mixtures thereof.

The solvents may be present in proportions preferably of between 1% and 40% by weight and even more preferentially between 5% and 30% by weight approximately relative to the total weight of the dye composition.

These compositions may also contain various adjuvants conventionally used in hair dye compositions, such as anionic, cationic, nonionic, amphoteric or zwitterionic surfactants or mixtures thereof, anionic, cationic, nonionic, amphoteric or zwitterionic polymers or mixtures thereof, mineral or organic thickeners, and in particular anionic, cationic, nonionic and amphoteric polymeric associative thickeners, antioxidants, penetrants, sequestrants, fragrances, buffers, dispersants, conditioning agents, for instance volatile or non-volatile, modified or unmodified silicones, film-forming agents, ceramides, preserving agents and opacifiers.

The above adjuvants may be present in an amount for each of them of between 0.01% and 20% by weight relative to the weight of the composition.

Needless to say, a person skilled in the art will take care to select this or these optional additional compound(s) such that the advantageous properties intrinsically associated with these compositions are not, or are not substantially, adversely affected by the envisaged addition(s).

These compositions may be in various forms, such as in the form of liquids, creams or gels, or in any other suitable cosmetic form.

The aqueous composition comprising hydrogen peroxide and at least 20% by volume of inert particles is acidic with a pH of less than 7, preferably between 1 and 7 and even more preferentially between 1.5 and 6. The pH may be adjusted to the desired value by means of acidic or alkaline agents usually used in cosmetics, or alternatively using standard buffer systems.

Among the acidic agents, examples that may be mentioned include mineral or organic acids, for instance hydrochloric acid, orthophosphoric acid or sulfuric acid, carboxylic acids, for instance acetic acid, tartaric acid, citric acid or lactic acid, and sulfonic acids.

Among the alkaline agents, examples that may be mentioned include aqueous ammonia, alkaline carbonates, alkanolamines such as diethanolamine and triethanolamine and also derivatives thereof, sodium hydroxide, potassium hydroxide and the compounds of formula (IV) below:

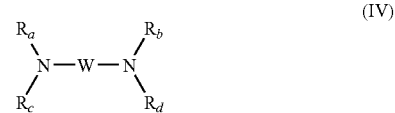

(IV)

in which W is a propylene residue optionally substituted with a hydroxyl group or a $C_1$-$C_4$ alkyl radical; $R_a$, $R_b$, $R_c$ and $R_d$, which may be identical or different, represent a hydrogen atom or a $C_1$-$C_4$ alkyl or $C_1$-$C_4$ hydroxyalkyl radical.

The compositions applied to the keratin fibres, resulting from the mixing of the aqueous composition comprising hydrogen peroxide and at least 20% by volume of inert particles with the composition(s) comprising the alkaline agent(s) and/or the persalt(s) and/or the direct dye(s) and/or the oxidation dye precursor(s) have a pH of between 4 and 12 and preferably between 7 and 11.

A subject of the present invention is also a kit for bleaching keratin fibres, characterized in that it contains at least two compositions, one of the compositions being an aqueous composition comprising hydrogen peroxide and at least 20% by volume of inert particles as defined above, and the compositions as a whole comprising at least one alkaline agent and/or at least one persalt and/or at least one dye precursor and/or at least one dye as defined above.

According to one particular embodiment of the invention, the kit in accordance with the invention contains an aqueous composition comprising hydrogen peroxide and at least 20% by volume of inert particles as defined above and an aqueous composition comprising at least one alkaline agent as defined above.

According to another particular embodiment of the invention, the kit in accordance with the invention contains an aqueous composition comprising hydrogen peroxide and at least 20% by volume of inert particles as defined above, an anhydrous composition comprising at least one persalt as defined above and an aqueous composition comprising at least one alkaline agent as defined above.

According to another particular embodiment of the invention, the device in accordance with the invention contains an aqueous composition comprising hydrogen peroxide and at least 20% by volume of inert particles as defined above, and an anhydrous composition comprising at least one alkaline agent and at least one persalt as defined above.

According to another particular embodiment of the invention, the device in accordance with the invention contains an aqueous composition comprising hydrogen peroxide and at least 20% by volume of inert particles as defined above and an aqueous composition comprising at least one direct dye as defined above.

According to another particular embodiment of the invention, the device in accordance with the invention contains an aqueous composition comprising hydrogen peroxide and at least 20% by volume of inert particles as defined above, an aqueous composition comprising at least one alkaline agent as defined above and an aqueous composition comprising at least one direct dye and/or at least one oxidation dye precursor as defined above.

According to another particular embodiment of the invention, the device in accordance with the invention contains an aqueous composition comprising hydrogen peroxide and at least 20% by volume of inert particles as defined above and an aqueous composition comprising at least one alkaline agent and at least one direct dye and/or at least one oxidation dye precursor as defined above.

According to another particular embodiment of the invention, the device in accordance with the invention contains an aqueous composition comprising hydrogen peroxide and at least 20% by volume of inert particles as defined above, an anhydrous composition comprising at least one alkaline agent and at least one persalt as defined above and an aqueous composition comprising at least one direct dye as defined above.

According to another particular embodiment of the invention, the device in accordance with the invention contains an aqueous composition comprising hydrogen peroxide and at least 20% by volume of inert particles as defined above, an anhydrous composition comprising at least one persalt as defined above, an aqueous composition comprising at least one alkaline agent as defined above and an aqueous composition comprising at least one direct dye as defined above.

A subject of the present invention is also the use for bleaching keratin fibres of a composition in accordance with the invention as defined above.

The examples that follow serve to illustrate the invention without, however, being limiting in nature.

EXAMPLE

The oxidizing composition 1 below was prepared:

| OXIDIZING COMPOSITION 1 | |
|---|---|
| Titanium oxide | 50 g |
| Sodium lauryl sulfate | 2 g |
| Oxyethylenated (100 OE) stearyl alcohol or Steareth-100 | 1 g |
| Ammonium acryloyldimethyltaurate/Steareth-25 methacrylate crosspolymer | 2 g |
| Sodium stannate, 6 H$_2$O | 0.04 g |
| Diethylenetriaminepentaacetic acid | 0.015 g |
| Tetrasodium pyrophosphate, 10 H$_2$O | 0.03 g |

| -continued | |
|---|---|
| OXIDIZING COMPOSITION 1 | |
| Hydrogen peroxide | 6 g |
| Phosphoric acid | qs pH = 3 |
| Demineralized water | qs 100 g |

The oxidizing composition 1 is mixed at the time of use with the bleaching powder 3, containing 50% persulfates, 24.1% silicates and 2.6% ammonium chloride, in a bleaching powder/oxidizing composition ratio equal to 1/1.5.

By way of reference, the oxidizing composition 2, containing 6% hydrogen peroxide and having a pH of 2, is mixed at the time of use with the bleaching powder 3 in a bleaching powder/oxidizing composition ratio equal to 1/1.5.

The mixtures obtained are applied to 2.5 g locks of natural chestnut-brown hair, at a rate of 10 g of mixture per 1 g of hair. After a leave-in time of 40 minutes, the locks are rinsed, washed with a standard shampoo, rinsed again and then dried.

The results are described in the table below.

| COMPARISON OF THE LEVELS OF BLEACHING | | |
|---|---|---|
| | Mixture 1 + 3 (invention) | Mixture 2 + 3 (prior art) |
| Bleaching effect | 5 tones | 4.5 tones |

It is found that the oxidizing composition in accordance with the invention makes it possible to obtain greater lightening than the known oxidizing composition of the prior art.

The invention claimed is:

1. An aqueous composition for bleaching keratin fibres comprising, in a cosmetically acceptable medium, hydrogen peroxide and at least 20% by volume of inert particles chosen from particles of titanium oxides, zinc oxides, carbonates, silicates, sulfides, polyamides, polyesters, polystyrenes, polyurethanes, polycyanoacrylates, polyethylenes, polymethyl methacrylates, polypropylenes, polycarbonates, Teflon, silicone elastomers, waxes, and complex synthetic compounds, wherein the composition has a viscosity of less than $2\times10^3$ poises at 25° C. and wherein the size of the inert particles ranges from 5 nm to 500 µm.

2. The composition according to claim 1, wherein the viscosity is between 0.1 and $2\times10^3$ poises at 25° C.

3. The composition according to claim 1, wherein the complex synthetic compounds are chosen from ceramic powders, zeolites, and glasses.

4. The composition according to claim 1, wherein the size of the inert particles ranges from 10 nm to 100 µm.

5. The composition according to claim 1, wherein the concentration of hydrogen peroxide ranges from 1% to 20% by weight relative to the total weight of the composition.

6. The composition according to claim 5, wherein the concentration of hydrogen peroxide ranges from 2% to 12% by weight relative to the total weight of the composition.

7. The composition according to claim 1, further comprising at least one surfactant, wherein the at least one surfactant comprises at least one fatty chain containing at least 8 carbon atoms.

8. The composition according to claim 7, wherein the at least one surfactant is chosen from anionic, nonionic, cationic, and amphoteric surfactants.

9. The composition according to claim 7, wherein the at least one surfactant is present in an amount ranging from 0.01% to 40% by weight relative to the total weight of the composition.

10. The composition according to claim 1, further comprising at least one associative or non-associative thickening polymer.

11. The composition according to claim 10, wherein the at least one thickening polymer is present in an amount of less than or equal to 10% by weight relative to the total weight of the composition.

12. The composition according to claim 1, further comprising at least one alkaline agent.

13. The composition according to claim 12, wherein the at least one alkaline agent is chosen from organic amines, ammonia, and silicates.

14. The composition according claim 1, further comprising at least one persalt.

15. The composition according to claim 14, wherein the at least one persalt is chosen from ammonium and alkali metal perborates, percarbonates, and persulfates.

16. The composition according to claim 1, further comprising at least one dye precursor and/or at least one direct dye.

17. The composition according to claim 16, wherein the at least one dye precursor is chosen from oxidation bases and/or couplers.

18. A process for bleaching keratin fibres, comprising applying to keratin fibres an aqueous composition for bleaching keratin fibres comprising, in a cosmetically acceptable medium, hydrogen peroxide and at least 20% by volume of inert particles chosen from particles of titanium oxides, zinc oxides, carbonates, silicates, sulfides, polyamides, polyesters, polystyrenes, polyurethanes, polycyanoacrylates, polyethylenes, polymethyl methacrylates, polypropylenes, polycarbonates, Teflon, silicone elastomers, waxes, and complex synthetic compounds, wherein the composition has a viscosity of less that $2 \times 10^3$ poises at 25° C. and wherein the size of the inert particles ranges from 5 nm to 500 μm.

19. A kit for bleaching keratin fibres, comprising at least two compositions, wherein one of the compositions is an aqueous composition for bleaching keratin fibres comprising, in a cosmetically acceptable medium, hydrogen peroxide and at least 20% by volume of inert particles chosen from particles of titanium oxides, zinc oxides, carbonates, silicates, sulfides, polyamides, polyesters, polystyrenes, polyurethanes, polycyanoacrylates, polyethylenes, polymethyl methacrylates, polypropylenes, polycarbonates, Teflon, silicone elastomers, waxes, and complex synthetic compounds, wherein the composition has a viscosity of less than $2 \times 10^3$ poises at 25° C. and wherein the size of the inert particles ranges from 5 nm to 500 μm.

20. The kit according to claim 19, wherein the second composition is chosen from at least one alkaline agent, persalt, dye precursor, and/or direct dye.

* * * * *